United States Patent [19]

Knifton et al.

[11] Patent Number: 5,162,592
[45] Date of Patent: Nov. 10, 1992

[54] ONE-STEP SYNTHESIS OF METHYL T-BUTYL ETHER FROM T-BUTANOL USING MULTIMETAL-MODIFIED ZEOLITE CATALYSTS

[75] Inventors: John F. Knifton, Austin; John R. Sanderson, Leander; Peishing E. Dai, Port Arthur, all of Tex.

[73] Assignee: Texaco Chemical Company, White Plains, N.Y.

[21] Appl. No.: 796,987

[22] Filed: Nov. 25, 1991

[51] Int. Cl.$^5$ .............................................. C07C 41/09
[52] U.S. Cl. .................................................. 568/698
[58] Field of Search ........................................ 568/698

[56] References Cited

U.S. PATENT DOCUMENTS 3,140,252  7/1964  Frilette et al. ........................ 568/698

Primary Examiner—Howard T. Mars
Attorney, Agent, or Firm—Jack H. Park; Kenneth R. Priem; Cynthia L. Kendrick

[57] ABSTRACT

Disclosed is an improved process for preparing methyl t-butyl ether in one step which comprises reacting tertiary butanol and methanol in the presence of a catalyst comprising a zeolite modified with a metal selected from the group consisting of Groups IB, VB, VIB, VIIB or VIII of the Periodic Table at a temperature of about 20° C. to 250° C. and atmospheric pressure to about 1000 psig, wherein when the temperature is in the operating range above about 160° C., the product comprises a two-phase mix of an isobutylene-MTBE product-rich phase and a heavier aqueous methanol-rich phase.

20 Claims, No Drawings

ONE-STEP SYNTHESIS OF METHYL T-BUTYL ETHER FROM T-BUTANOL USING MULTIMETAL-MODIFIED ZEOLITE CATALYSTS

CROSS-REFERENCE

This application is related to U.S. Pat. Nos. 4,827,048 and 4,822,921 and to application Ser. Nos. 07/494,280, 07/724,071 and 07/494,281 and to Ser. Nos. 07/677,192 and 07/663,527 (both allowed, but not issued).

It is also related to copending U.S. Ser. No. 07/724,071; 07/745,177 and 07/783,015.

This invention concerns an improved process for preparing methyl tertiary-butyl ether (MTBE) in one step by the reaction of tertiary butanol and methanol in the presence of a catalyst comprising a zeolite modified with a metal selected from the group consisting of Groups IB, VB, VIB, VIIB and VIII of the Periodic Table as defined in the Condensed Chemical Dictionary, page 789. Metals which work well include transition metals found in Row 1 of Groups IB, VIB and VIII, particularly iron, copper, chromium and nickel. The invention is especially advantageous in that the multimetal-modified zeolites exhibit both high activity during methyl t-butyl ether synthesis from methanol plus t-butanol and, additionally, exhibit concurrent quantitative peroxide decomposition of, for example di-t-butyl peroxide (DTBP), in the alcohol feedstock.

BACKGROUND OF THE INVENTION

It is known to those skilled in the art that ethers including unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether is finding increasing use as a blending component in high octane gasoline as the current gasoline additives based on lead and manganese are phased out. Currently all commercial processes for the manufacture of methyl tert-butyl ether are based upon the liquid-phase reaction of isobutylene and methanol (Eq. 1), catalyzed by a cationic ion-exchange resin (see, for example: Hydrocarbon Processing, Oct. 1984, p. 63; Oil and Gas J., Jan. 1, 1979, p. 76; Chem. Economics Handbook-SRI, September 1986, p. 543-7051P). The cationic ion-exchange resins used in MTBE synthesis normally have the sulphonic acid functionality (see: J. Tejero, J. Mol. Catal., 42 (1987) 257; C. Subramamam et al., Can. J. Chem. Eng., 65 (1987) 613).

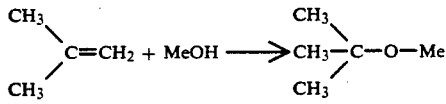

(Eq. 1)

With the expanding use of MTBE as an acceptable gasoline additive, a growing problem is the availability of raw materials. Historically, the critical raw material is isobutylene (Oil and Gas J., Jun. 8, 1987, p. 55). It would be advantageous, therefore, to have a process to make MTBE that does not require isobutylene as a building block. It would be advantageous to have an efficient process for making MTBE by reaction of methanol with tertiary butyl alcohol, since t-butanol (TBA) is readily available commercially through isobutane oxidation.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl. Vses Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any major problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

Japanese Patent 0007432 teaches the use of zeolites to make dialkyl ethers containing primary or secondary alkyl groups. The zeolites have a porous structure and are represented by:

$$M_2/O.Al_2O.xSiO_2.yH_2O$$

where M is an alkali metal or alkaline earth metal cation or organic base cation, n is the valence of the cation and x and y are variables.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In copending U.S. patent application Ser. No. 07/494,281, there is disclosed a method for preparing methyl tertiary butyl ether by reacting butanol and methanol in the presence of a catalyst comprising a super-acid alumina or a faujasite-type zeolite.

In copending U.S. patent application Ser. No. 07/663,527, a Y-type zeolite modified with fluorosulfonic acid is disclosed.

Some of the limitations present in the catalyst systems described above include loss of activity at temperatures above 120° C., deactivation due to the presence of peroxides in the feedstock, lower than desirable selectivity and the requirement of multiple steps to accomplish the synthesis and separation of the product.

It would represent a distinct advance in the art if tertiary butanol, instead of isobutylene, and methanol could be reacted to form MTBE in one-step over a modified zeolite catalyst which exhibited the ability to withstand elevated temperatures, an extended useful life and allowed for improved selectivity for the desired product even in the presence of peroxides. It would also be very useful if crude product phase separation were possible. In addition, it would be very useful in the art if a catalyst which allowed for increased MTBE plus isobutylene selectivity also contributed to decomposition of peroxides, such as di-t-butyl peroxide (DTBP), which may be present in the alcohol feedstock.

SUMMARY OF THE INVENTION

In accordance with certain of its aspects, the novel method of this invention for preparing methyl tert-butyl ether (MTBE) from tertiary butyl alcohol (t-butanol or TBA) and methanol (MeOH) in one-step comprises reacting tertiary butyl alcohol and methanol in the presence of a catalyst comprising a multimetal-modified zeolite at an elevated temperature and moderate pressure. Examples demonstrate particularly the effectiveness of an iron, copper, nickel, manganese and chromium-modified zeolite.

DESCRIPTION OF THE INVENTION

Preparation of the product of this invention may be carried out typically by reacting tertiary butyl alcohol and methanol in the presence of an etherification catalyst. The etherification is carried out in one-step and the catalyst preferably comprises a rare earth-exchanged or ammonium-exchanged Y-zeolite modified with one or more metals selected from the group consisting of Group IB, VB, VIB, VIIB or VIII of the Periodic Table.

The reaction can be represented by the following:

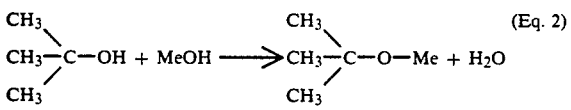
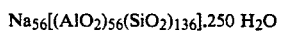

Generally the methanol and t-butanol coreactants may be mixed in any proportion in order to generate the desired methyl t-butyl ether, but preferably the molar ratio of methanol to t-butanol in the feed mixture should be between 10:1 and 1:10, if the yield of desired MTBE is to be maximized. In order to achieve maximum selectivity to MTBE, and optimum conversion per pass, an excess of methanol in the liquid feed is desirable. The most preferred methanol-to-tertiary butanol molar ratio is from 1:1 to 5:1.

In certain circumstances, it may be particularly desirable that the TBA conversion be high enough (e.g. 80% or greater), such that the crude product mix phase separates into an isobutylene-MTBE product-rich phase and a heavier aqueous methanol phase. Preferably such a product phase separation would be achieved at as low an etherification temperature as possible, but it is particularly observed in the range 160°–200° C.

The synthesis of Eq. 2 can also be conducted where the t-butanol and methanol reactants are mixed with certain other components including water, ketones such as acetone (Ac$_2$O), peroxides and hydroperoxides such as di-t-butyl peroxide (DTBP) and allyl t-butyl peroxide (ATBP), and t-butyl hydroperoxide (TBHP), as well as esters such as t-butyl formate (TBF). Typically each of said classes of components makes up less than 10% of the total feed mixture.

It has been discovered in the instant invention that the multimetal-modified zeolite catalysts herein disclosed function to exhibit concurrent quantitative decomposition of peroxide in the alcohol feedstock in addition to converting tertiary butanol plus methanol to MTBE. This constitutes an important advantage in a commercial setting.

The instant one-step process may also be applied to the preparation of other alkyl tertiary alkyl ethers. For example, process may be applied to the reaction of a $C_1$–$C_6$ primary alcohol such as methanol, ethanol, n-propanol and n-hexanol with a $C_4$–$C_{10}$ tertiary alcohol such as, for example, tertiary butanol and tertiary amyl alcohol. Reaction of methanol with tertiary amyl alcohol (2-methyl-2-butanol) would then yield methyl tertiary amyl ether (TAME). Alternatively a mixture of alcohols, e.g., a mixture of $C_1$–$C_5$ alcohols, could be reacted to give a mixture of alkyl tert-alkyl ethers.

In the modified catalyst of the instant invention good results were realized using certain crystalline aluminosilicate zeolites as catalysts for the reaction represented in Eq. 2. Particularly effective were the isostructural group of faujasite zeolites that include the synthetic Y-zeolites. The preferred catalysts were the rare-earth exchanged or ammonium exchanged Y-zeolites modified with multiple metals.

The unit cells of zeolites X and Y are cubic, $a_o \leq 2.5$ nm, and each contains 192 silicon- or aluminum-centered oxygen tetrahedra which are linked through shared oxygen atoms. Because of the net negative charge on each of the aluminum-centered tetrahedra, each unit cell contains an equivalent number of charge-balancing cations. These are exclusively sodium ions in zeolites in their synthesized form. Typical cell contents for the Y-zeolites in the hydrated form are:

$$Na_{56}[(AlO_2)_{56}(SiO_2)_{136}] \cdot 250\ H_2O$$

Y-zeolites are distinguished on the basis of the relative concentration of silicon and aluminum atoms and the consequent effects on detailed structure and related chemical and physical properties. The aluminum atoms in the unit cell of Y-zeolite vary from 76 to 48 giving a Si:Al ratio between 1.5 and 3.0. Both the cation concentration and charge density on the aluminosilicate structure are lower for Y-zeolites than for X-zeolites, where the aluminum atoms in the unit cell vary from 96 to 77.

The feature which determines the difference between faujasites and other zeolites built up from sodalite units is the double 6-membered ring or hexagonal prism, by which the units are linked. The sodalite unit, or β-cage, can be represented by a truncated octahedron, with the 24 silicon or aluminum atoms (designated T atoms) taking positions at the vertices. The 36 oxygen atoms are displaced from the midpoints of the edges joining the vertices in order to attain tetrahedral configuration around the T atoms. The free diameter of the void within the β-cage is 0.66 nm, but only the smallest molecules can enter through the 0.22 nm diameter opening in the distorted ring of six oxygen atoms associated with each hexagonal face. Each sodalite unit is linked tetrahedrally across hexagonal faces by six bridging oxygens to four other sodalite units. The larger void spaces enclosed by sodalite units and hexagonal prisms are termed α-cages, or supercages. The α-cage is a 26-hedron with a free diameter of ≈1.3 nm, and it can be entered through four distorted 12-member rings of diameter 0.80–0.90 nm. In this way each α-cage is tetrahedrally joined to four others giving a complex system of void space extending throughout the zeolite structure. The α- and β-cages together give Y-zeolites, along with X-zeolites, the largest void volume of any known zeolites, which is ca. 50 vol % of the dehydrated crystal.

From the catalytic viewpoint, the α-cages are by far the most important, since, unlike the β-cages, they permit entry of numerous aliphatic and aromatic compounds.

Particularly effective in the subject synthesis of MTBE are the synthetic Y-zeolites modified with multiple metals. Preferably said zeolites should be in a strongly acidic form whereby some, or all, of the cations (Group I or II, alkali or alkaline earth metal ions such as sodium, potassium, calcium or magnesium) are exchanged by protons either through ammonium exchange followed by thermal stabilization (deammoniation, removal of $NH_3$) at elevated temperatures (e.g. 400°–500° C.) through mineral acid treatment, etc. Alternatively, said Y-zeolites may be dealuminized by hydrothermal treatment, or by treatment with ethylenediaminetetraacetic acid (EDTA) or other chelating agents, in which case said dealuminized Y-zeolites should have a Si:Al ratio of greater than unity but preferably in the range 3 to 100. A further possibility is that said Y-zeolites may be rare-earth exchanged with, for example, a mixture of rare-earth salts, by treatment with lanthanum salts, etc. Said rare-earth exchanged Y-zeolites may then have a Si:Al ratio of 1.5 to 3. The exchange of the sodium ions of the Y-zeolite by rare earth ions has been reviewed (see, for example, R. Rudham and A. Stockwell, The Chemical Society Specialist Periodical Report—Catalysis, Vol. I, 1977, Chapter 3).

Illustrative of suitable Y-zeolites for the practice of this invention include Linde SK-500, a rare-earth exchanged Y-zeolite, having a Si:Al ratio of 1.5→2, compounded with 10–20% added alumina binder as 1/16" diameter extrudates and UOP's LZY-62, an ammonium-exchanged Y-zeolite, thermally stabilized at 500° C., having a silica:alumina ratio of about 1.5–2.2:1, as well as CP316-26, an ammonium exchanged Y-zeolite this time having a silica-to-alumina ratio of 46, and a unit cell size of 24.26A, marketed by PQ Corporation.

The metals useful for modifying the zeolite in the instant invention comprise those from Group IB, VB, VIB, VIIB and VIII of the Periodic Table, including transition metals. Preferred metals are those found in Row 1 of Groups IB, VIB and VIII of the Period Table. Especially good results were observed using iron, copper and chromium or nickel, copper and chromium on VALFOR® zeolite CP316-26. Other multimetal-modified zeolites which exhibited good properties included iron, copper, chromium and cobalt, manganese on LZY-62 zeolite and Ni, Cu, Cr on SK-500 zeolite.

Examples 1–4 demonstrate the preparation of the multimetal-modified catalysts. Salts of iron, nickel, copper and chromium, such as acetonates or nitrates were dissolved in acetone and the zeolites were added, most often, in the form of extrudates. The catalysts were then calcined by heating to 400°–450° C. and optionally reduced in a stream of hydrogen at 200° C.

The amount of the various metals deposited on the zeolite can vary. The amount of each individual metal, iron, chromium, copper, manganese, and nickel, can vary from 0.01 to 10.0%. Where iron, chromium and copper are deposited on CP316-26 the preferred weight percent is from 0.01% to 1.0%. In the case where iron, chromium, and copper are deposited on LZY-62 the weight percent of the various metals is in the range from about 0.01% to 2.0%. Where nickel, copper, chromium are deposited to SK-500 or CP316-26, the wt % of the various metals is in the range 0.01% to 10%.

Said catalysts may be in the form of powders, pellets, granules, spheres, shapes and extrudates. The examples described herein demonstrate the advantages of using extrudates.

The reaction may be carried out in either a stirred slurry reactor or in a fixed bed continuous flow reactor. The catalyst concentration should be sufficient to provide the desired catalytic effect.

Etherification can generally be conducted at temperatures from 20° to 250° C.; the preferred range is 80° to 200° C. Good results are observed throughout this temperature range. However, it can be noted that the best conversion figures for DTBP and tert-butanol are observed when the temperature is around 160° C. or higher. The total operating pressure may be from 0 to 1000 psig, or higher. The preferred pressure range is 50 to 500 psig.

Typically, MTBE is generated continuously in up to ca. 40 wt % concentration or greater in the crude liquid product at total liquid hourly space velocities (LHSV) of up to 6 or higher and relatively mild conditions, where:

$$LHSV = \frac{\text{Volume Of Liquid Feed Run Through The Reactor Per Hour}}{\text{Volume of Catalyst In Reactor}}$$

Conversions of t-butanol (TBA, wt %) are estimated in the following examples using the equation:

$$\frac{(\text{Mole \% of } TBA \text{ in Feed} - \text{Mole \% of } TBA \text{ in Product})}{\text{Mole \% of } TBA \text{ in Feed}} \times 100$$

Conversions of peroxide are estimated using the equation:

$$\frac{(\text{Mole \% } DTBP \text{ in Feed} - \text{Mole \% } DTBP \text{ in Product})}{\text{Mole \% } DTBP \text{ in Feed}} \times 100$$

As noted in Examples 10–11, the conversion of DTBP reaches a high of 99%. Selectivities of methyl t-butyl ether (MTBE, mole %) and isobutylene ($C_4H_8$, mole %) are estimated from:

$$\frac{\text{Moles of } MTBE \text{ (or } C_4H_8 \text{ in Product)}}{\text{moles of } TBA \text{ converted}} \times 100$$

The examples which follow illustrate the one-step synthesis of MTBE from TBA and MeOH (Eq. 2) using 15 multimetal-modified Y-type zeolites particularly the form of extrudates. The examples are only intended as a means of illustration and it is understood the invention is not meant to be limited thereby.

The accompanying examples illustrate:

1) Examples 1–4 serve to show the synthesis of four multimetal-modified zeolites including:
Fe, Cu, Cr on VALFOR® CP316-26
Fe, Cu Cr on LZY-62
Ni, Cu, Cr on SK-500
Ni, Cr, Cr on VALFOR® CP316-26

2) Example 5 illustrates the cosynthesis of MTBE and isobutylene via etherification with methanol/t-butanol feedstock using the Fe, Cu, Cr on VALFOR® CP316-26 zeolite catalyst of Example 1.

Here:
At 120° C.: TBA Conversion=68% MTBE and isobutylene selectivities are 74 and 21% respectively.
At 160° C.: TBA Conversion=90% Product phase separation is achieved giving an isobutylene- MTBE rich phase and a heavier aqueous methanol phase.

3) In Examples cosynthesis of MTBE plus isobutylene is achieved with the catalysts of Examples 2-4. Here of note is the fact that the Ni, Cu, Cr-modified zeolite CP316-26 of Example 4 gives in Example 8, ca. 80% TBA conversion at 160° C. and also product phase separation at the same temperature.

4) Example 9 serves to demonstrate the cosynthesis of MTBE and isobutylene via methanol/t-butanol etherification using a crude feedstock containing water, MTBE and 2.5% di-t-butyl peroxide over the Fe, Cu, Cr on CP316-26 catalyst of Example 1 using a series of operating temperatures and space velocities. Of particular note, concurrent quantitative DTBP decomposition is achieved, typically at 160° C., LHSV=1, where TBA conversion is ≧70% per pass. There is no detectable Fe, Cu, Cr in the effluent.

5) Similar results are illustrated in Examples 10 and 11 for the Fe, Cu, Cr on LZY-62 and Co, Mn on LZY-62 zeolites.

6) Example 12 illustrates the production of MTBE plus isobutylene, with concurrent DTBP decomposition, using another crude feedstock having ca. 2:1 molar ratio of methanol, t-butanol and 4.4% DTBP. Again the catalyst is the Fe, Cu, Cr modified CP316-26 of Example 1.

EXAMPLE 1

Preparation of Catalyst Fe, Cu, Cr on VALFOR ® 316-26 1/16" E

Ferrous acetylacetonate (4.0 g), cupric acetylacetonate (4.0 g) and chromium acetylacetonate (4.0 g) were dissolved in 500 g acetone. This solution was stirred for an hour and added to 400 g VALFOR ® 316-26 1/16" diameter extrudates. The acetone was then removed on a rotary evaporator. The catalyst was then charged to a reactor and heated to 200° C. and purged with air overnight. The reactor was then heated to 400° C. and purged with air overnight. The catalyst was then cooled to 200° C. under nitrogen. Hydrogen was slowly added until the purge was 100% hydrogen. The temperature was maintained at 200° C. for 3 hours with 100% hydrogen. The catalyst was then placed in a stoppered bottle until it was used. Analysis by atomic absorption (AA) showed: Fe=0.12%, Cr=0.10%, and Cu=0.02%.

EXAMPLE 2

Preparation of Catalyst Fe, Cu, Cr on LZY-62, 1/16" E

Following the procedures of Example 1, a sample of LZY-62, 1/16" extrudates were treated with an acetone solution of ferrous acetylacetonate, cupric acetylacetonate and chromium acetylactonate, excess acetone removed and the catalyst then heated in stages to 400° C. in a stream of air, followed by reduction under flow of hydrogen at 200° C.

Analyses of the formed catalyst showed: Fe =0.87%, Cr=0.73%, and Cu 1.7%.

EXAMPLE 3

Preparation of Catalyst, Ni, Cu, Cr on SK-500, 1/16" E

Nickel nitrate (50.7 g), chromium nitrate (39.3 g) and copper nitrate (18.7 g) were melted to about 70° C. and distilled water added to make up a total volume of 130-150 ml. About half of this solution was impregnated into a sample of Linde SK-500 (150 g) and the wetted support then dried at about 120° C. overnight. The dried support was then impregnated with the second half of the nickel-copper-chromium solution, dried again at 120° C. for 4 hours, and calcined at ca. 450° C. for 6 hours.

Analysis of the formed catalyst showed: Ni=5.2%; Cr=2.5%; Cu=1.2%.

EXAMPLE 4

Preparation of Catalyst Ni, Cu, Cr on CP316-26

Following the procedures of Example 3, a sample of CP316-26, 1/16" extrudates were treated with an aqueous solution of nickel nitrate, chromium nitrate and copper nitrate, the impregnated zeolite dried at 120° C. and then calcined at ca. 450° C. for 6 hours.

Analyses of the formed catalyst show: Ni=5.4%; Cr=2.5%; Cu 2.7%.

EXAMPLE 5

This example illustrates the production of methyl t-butyl ether from t-butanol and methanol using the Fe, Cu, Cr impregnated CP316-26 zeolite of Example 1.

Synthesis was conducted in a tubular reactor (½" id, 12" long), constructed of 316 stainless steel, operated upflow and mounted in a furnace, controllable to ±1.0° C. and fitted with pumps allowing flow control to <±1 cc/hr. The reactor was also fitted with a pressure regulating device and equipment for monitoring temperature, pressure and flow rate.

The reactor was charged at the beginning of the experiment with 25 cc of Fe, Cu, Cr treated zeolite, CP316-26, prepared by the procedure of Example 1, as 1/16" extrudates. A screen of glass wool was placed at the top and the bottom of the reactor to ensure the catalyst would remain in the middle portion.

The catalyst bed was treated with a methanol/t-butanol (1.1:1 molar mix) upflow, at a rate of 50 cc/hr, while the reactor was held at 120° C., with a total pressure of 300 psi. Samples of crude product effluent were collected periodically on stream, in 316 ss bombs, and analyzed by glc.

Typical analyses data for samples taken under these conditions are summarized in Table I. Concentrations of MTBE, isobutylene, methanol, and t-butanol in the product effluent were also measured at a series of higher temperatures (140°-180° C.). These data are also included in Table I.

| For Sample #1, at 120° C.: | |
|---|---|
| TBA Conversion | 68% |
| MTBE Selectivity | 74% |
| Isobutylene Selectivity | 21% |
| For Sample #5, at 160° C.: | |
| TBA conversion | ca. 90% |

The crude liquid product separates into two phases, an isobutylene-MTBE product-rich and a heavier, aqueous methanol, phase.

EXAMPLES 6-8

Using the equipment and following the procedures of Example 5, the multimetal-impregnated zeolite catalysts of Examples 2-4 were treated with a 1.1:1 molar mix of methanol to t-butanol at a series of operating temperatures, from 120° C. to 180° C.

Concentrations of MTBE, isobutylene, methanol and t-butanol in the product effluent under the specific conditions, as determined by glc for each catalyst, are summarized in the accompanying Tables II to IV.

Of particular note:

a) In Example 8 and Table IV, using the Ni, Cu, Cr-modified zeolite CP316-26 catalysts of Example 4:

For Sample #6 at 160° C.
TBA Conversion=ca. 80%

The crude liquid product is separated into two phases, an isobutylene-MTBE product-run phase and a heavier, aqueous methanol, phase.

b) In Example 7 and Table III, using the Fe, Cr, Cu-treated zeolite LYZ-62 catalyst of Example 2:

| For Sample #5 at 160° C. | |
|---|---|
| TBA Conversion | 80% |
| MTBE Selectivity | 43% |
| Isobutylene Selectivity | 56% |

TABLE I

MTBE From MEOH/TBA

| Ex. | Catalyst | MeOH/TBA Molar Ratio | Temp. (°C.) | Feed Rate (cc/hr) | Time On Stream (Days) | SAMPLE | H₂O | MeOH | C₄H₈ | TBA | MTBE |
|---|---|---|---|---|---|---|---|---|---|---|---|
| 5 | Ex. 1 | | | | | FS-1 | | 32.3 | | 67.3 | |
| | | 1.1 | 120 | 50 | 1 | →1 | 10.6 | 20.4 | 7.3 | 21.5 | 40.0 |
| | | | | | | 2 | 10.5 | 20.4 | 7.2 | 21.6 | 39.9 |
| | | | 140 | 50 | 2 | 3 | 11.8 | 22.3 | 12.9 | 17.0 | 35.6 |
| | | | | | | 4 | 11.4 | 21.5 | 12.9 | 18.0 | 36.0 |
| | | | 160 | 50 | 3 | →5 { | 3.0 | 13.6 | 48.7 | 5.3 | 29.1 |
| | | | | | | | 30.2 | 43.9 | 5.9 | 7.9 | 10.7 |
| | | | | | | 6 { | 2.7 | 11.8 | 40.6 | 7.1 | 25.6 |
| | | | | | | | 29.9 | 44.5 | 5.9 | 8.4 | 11.0 |
| | | | 180 | 50 | 4 | 7 { | 0.9 | 5.9 | 71.7 | 1.5 | 18.4 |
| | | | | | | | 30.9 | 57.0 | 4.1 | 4.1 | 3.7 |
| | | | | | | 8 { | 0.5 | 7.4 | 73.7 | 4.5 | 13.7 |
| | | | | | | | 31.7 | 56.0 | 4.1 | 3.8 | 4.0 |

TABLE II

MTBE From MEOH/TBA

| Ex. | Catalyst | MeOH/TBA Molar Ratio | Temp. (°C.) | Feed Rate (cc/hr) | Time On Stream (Days) | SAMPLE | H₂O | MeOH | C₄H₈ | TBA | MTBE |
|---|---|---|---|---|---|---|---|---|---|---|---|
| 6 | Ex. 3 | | | | | FS-1 | | 32.7 | | 67.0 | |
| | | 1.1 | 120 | 50 | 1 | 1 | | 31.8 | | 66.3 | |
| | | | | | | 2 | 0.3 | 33.0 | 0.2 | 66.2 | 0.1 |
| | | | 140 | 50 | 2 | 3 | 1.2 | 31.2 | 1.7 | 62.0 | 3.6 |
| | | | | | | 4 | 1.1 | 31.5 | 1.3 | 62.9 | 3.0 |
| | | | 160 | 50 | 3 | 5 | 5.5 | 27.2 | 7.8 | 42.6 | 16.6 |
| | | | | | | 6 | 6.3 | 26.7 | 8.0 | 41.8 | 17.0 |
| | | | 180 | 50 | 4 | 7 | 12.3 | 24.5 | 21.5 | 17.2 | 24.3 |
| | | | | | | 8 | 12.3 | 24.1 | 22.6 | 16.3 | 24.4 |

TABLE III

MTBE From MEOH/TBA

| Ex. | Catalyst | MeOH/TBA Molar Ratio | Temp. (°C.) | Feed Rate (cc/hr) | Time On Stream (Days) | SAMPLE | H₂O | MeOH | C₄H₈ | TBA | MTBE |
|---|---|---|---|---|---|---|---|---|---|---|---|
| 7 | Ex. 2 | | | | | FS-1 | | 33.8 | | 65.9 | |
| | | 1.1 | 120 | 50 | 1 | 1 | 4.0 | 29.9 | 4.3 | 50.3 | 11.1 |
| | | | | | | 2 | 3.9 | 29.6 | 4.0 | 49.7 | 12.5 |
| | | | 140 | 50 | 2 | 3 | 9.2 | 23.9 | 10.4 | 26.2 | 29.9 |
| | | | | | | 4 | 9.7 | 24.3 | 9.8 | 27.7 | 28.3 |
| | | | 160 | 50 | 3 | →5 | 12.4 | 25.0 | 22.3 | 13.3 | 26.7 |
| | | | | | | 6 | 12.3 | 25.0 | 22.6 | 13.8 | 26.0 |
| | | | 180 | 50 | 4 | 7 { | 2.6 | 10.5 | 67.7 | 2.7 | 16.2 |
| | | | | | | | 29.2 | 53.9 | 5.8 | 5.2 | 5.5 |
| | | | | | | 8 { | 0.8 | 7.4 | 72.7 | 2.3 | 16.6 |
| | | | | | | | 28.8 | 54.7 | 6.1 | 5.0 | 5.0 |

TABLE IV

MTBE From MEOH/TBA

| Ex. | Catalyst | MeOH/TBA Molar Ratio | Temp. (°C.) | Feed Rate (cc/hr) | Time On Stream (Days) | SAMPLE | H₂O | MeOH | C₄H₈ | TBA | MTBE |
|---|---|---|---|---|---|---|---|---|---|---|---|
| 8 | Ex. 4 | | | | | FS-1 | | 32.9 | | 66.6 | |
| | | 1.1 | 120 | 50 | 1 | 1 | 1.1 | 31.8 | 0.9 | 63.3 | 2.5 |
| | | | | | | 2 | 0.8 | 31.5 | 0.7 | 63.8 | 2.8 |
| | | | 140 | 50 | 2 | 3 | 10.0 | 21.5 | 8.6 | 28.3 | 31.4 |
| | | | | | | 4 | 9.9 | 20.9 | 9.6 | 24.8 | 34.5 |
| | | | 160 | 50 | 3 | 5 { | 12.4 | 23.5 | 22.4 | 14.9 | 26.6 |
| | | | | | | | 30.4 | 36.8 | 6.6 | 12.8 | 13.2 |
| | | | | | | →6 { | 12.2 | 23.2 | 23.1 | 14.5 | 26.8 |
| | | | | | | | 30.4 | 36.9 | 6.7 | 12.4 | 13.3 |
| | | | 180 | 50 | 4 | 7 { | 0.9 | 7.9 | 69.1 | 3.2 | 18.7 |
| | | | | | | | 31.2 | 51.7 | 4.8 | 6.1 | 5.8 |
| | | | | | | 8 { | 2.3 | 10.2 | 65.0 | 3.6 | 18.6 |
| | | | | | | | 30.8 | 51.2 | 5.5 | 6.2 | 5.8 |

EXAMPLE 9

This example illustrates the decomposition of di-t-butyl peroxide in a t-butanol stream with concurrent MTBE formation when heated in the presence of the Fe, Cu, Cr impregnated CP316-26 zeolite of Example 1.

Synthesis was conducted in a tubular reactor (½" i.d., 29" long) constructed of 316 stainless steel, operated upflow and mounted in a furnace, controllable to ±1.0° C. and fitted with pumps allowing flow control to <±1 cc/hr. Pressure regulation was with a skinner uni-flow value and a foxboro controller.

The reactor was charged at the beginning of the experiment with 100 cc of Fe, Cu, Cr-treated zeolite CP316-26, prepared by the procedures of Example 1, as 1/16" extrudates. A screen of glass wool was placed at the top and bottom of the reactor to ensure the catalysts would remain in the middle portion.

The catalyst bed was treated with a feed mix comprising 10% water, 51% methanol, 35.5% t-butanol, 1.0% MTBE and 2.5% di-t-butyl peroxide, at a series of temperatures (120°–180° C.) and space velocities (LHSV=1→4). Samples of crude product effluent were collected periodically on stream, in 316 ss bombs, and analyzed by glc.

Typical analyses data are summarized in Table V show:

a) t-butanol (TBA) conversion to MTBE
b) MTBE plus isobutylene (IC₄H₈) formation from t-butanol plus methanol
c) Decomposition of the di-t-butyl peroxide (DTBP) Of Note, at 60° C. and LHSV = 1.

| | |
|---|---|
| DTBP Conversion | >99% |
| t-Butanol Conversion | 73% |

EXAMPLES 10–11

Using the equipment and following the procedures of Example 9, two multimetal-impregnated zeolite catalysts were treated with the feed mix comprising 10% water, 51% methanol, 35.5% t-butanol, 1.0% MTBE and 2.5% di-t-butyl peroxide at a series of temperatures (120°–180° C.) and space velocities (LHSV=1→4). The two catalysts comprised:

a) An Fe, Cu, Cr on LZY-62 prepared by the method of Example 2.
b) A Co, Mn on LZY-62 prepared by a method similar to Example 2.

Typical product effluent analyses for each catalyst are illustrated in the accompanying Tables VI and VII. Of particular note:

a) In Example 10 and Table VI, using the Fe, Cu, Cr-Modified LZY-62:

| | |
|---|---|
| At 160° C., LHSV | 1 |
| DTBP Conversion | >99% |
| TBA Conversion | 65% | b) In Example 11 and Table VII, using the Co, Mn Modified LZY-62:

| | |
|---|---|
| At 160° C., LHSV | 2 |
| DTBP Conversion | 99% |
| TBA Conversion | 69% |

TABLE V
SIMULTANEOUS DECOMPOSITION OF DTBP AND PREPARATION OF MTBE IN A CONTINUOUS REACTOR

| NOTEBOOK NUMBER | 6773-16-H | 6773-22-1 | 6773-22-2 | 6773-22-3 | 6773-22-4 |
|---|---|---|---|---|---|
| CATALYST | | VAL316-26 FE,CU,CR | VAL316-26 FE,CU,CR | VAL316-26 FE,CU,CR | VAL316-26 FE,CU,CR |
| REACTOR (CC) | | 100 | 100 | 100 | 100 |
| PRESSURE (PSIG) | | 500 | 500 | 500 | 500 |
| FEED RATE (cc/Hr.) | | 100 | 100 | 100 | 100 |
| TEMPERATURE (C.) | | 120 | 140 | 160 | 180 |
| TIME ON STREAM (HR) | | 5 | 5 | 5 | 5 |

TABLE V-continued
SIMULTANEOUS DECOMPOSITION OF DTBP AND PREPARATION OF MTBE IN A CONTINUOUS REACTOR

| | | | | | |
|---|---|---|---|---|---|
| SPACE VEL. (cc/cc) | | 1 | 1 | 1 | 1 |
| DTBP CONV. (%) | | 17.2 | 89.7 | 99.8 | 100.0 |
| TBA CONVERSION (%) | | 65.2 | 68.4 | 72.6 | 78.4 |
| IC$_4$H$_8$ | 0.003 | 0.987 | 3.142 | 4.864 | 2.300 |
| MEOH | 55.968 | 51.103 | 51.290 | 52.549 | 67.020 |
| ACETONE | 0.014 | 0.148 | 0.576 | 0.686 | 0.898 |
| MTBE | 1.236 | 31.053 | 30.041 | 25.392 | 16.134 |
| TBA | 39.848 | 13.857 | 12.602 | 10.931 | 8.621 |
| DTBP | 2.834 | 2.347 | 0.291 | 0.007 | 0.000 |
| NOTEBOOK NUMBER | 6773-16-H | 6773-23-1 | 6773-23-2 | 6773-23-3 | 6773-23-4 |
| CATALYST | | VAL316-26 W/FECUCR | VAL316-26 W/FECUCR | VAL316-26 W/FECUCR | VAL316-26 W/FECUCR |
| REACTOR (CC) | | 100 | 100 | 100 | 100 |
| PRESSURE (PSIG) | | 500 | 500 | 500 | 500 |
| FEED RATE (cc/Hr.) | | 200 | 200 | 200 | 200 |
| TEMPERATURE (C.) | | 120 | 140 | 160 | 180 |
| TIME ON STREAM (HR) | | 4 | 4 | 4 | 4 |
| SPACE VEL. (cc/cc) | | 2.0 | 2.0 | 2.0 | 2.0 |
| DTBP CONV. (%) | | 3.5 | 38.8 | 91.6 | 99.9 |
| TBA CONVERSION (%) | | 47.3 | 68.6 | 70.4 | 77.0 |
| IC$_4$H$_8$ | 0.003 | 1.362 | 4.057 | 3.876 | 3.651 |
| MEOH | 55.968 | 51.740 | 49.945 | 53.690 | 59.953 |
| ACETONE | 0.014 | 0.062 | 0.295 | 0.701 | 0.898 |
| MTBE | 1.236 | 22.750 | 30.507 | 26.777 | 19.561 |
| TBA | 39.848 | 21.015 | 12.524 | 11.780 | 9.153 |
| DTBP | 2.834 | 2.734 | 1.735 | 0.239 | 0.003 |
| NOTEBOOK NUMBER | 6773-16-H | 6773-24-1 | 6773-24-2 | 6773-24-3 | 6773-24-4 |
| CATALYST | | VAL316-26 /Fe,Cu,Cr | VAL316-26 /Fe,Cu,Cr | VAL316-26 /Fe,Cu,Cr | VAL316-26 /Fe,Cu,Cr |
| REACTOR (CC) | | 100 | 100 | 100 | 100 |
| PRESSURE (PSIG) | | 500 | 500 | 500 | 500 |
| FEED RATE (cc/Hr.) | | 400 | 400 | 400 | 400 |
| TEMPERATURE (C.) | | 120 | 140 | 160 | 180 |
| TIME ON STREAM (HR) | | 4 | 4 | 4 | 4 |
| SPACE VEL. (cc/cc) | | 4.0 | 4.0 | 4.0 | 4.0 |
| DTBP CONV. (%) | | 0.4 | 6.8 | 42.4 | 90.4 |
| TBA CONVERSION (%) | | 19.1 | 43.4 | 64.8 | 72.6 |
| IC$_4$H$_8$ | 0.003 | 0.840 | 1.940 | 2.034 | 3.495 |
| MEOH | 55.968 | 54.286 | 52.687 | 53.887 | 57.092 |
| ACETONE | 0.014 | 0.025 | 0.092 | 0.433 | 0.961 |
| MTBE | 1.236 | 9.579 | 19.722 | 26.515 | 23.384 |
| TBA | 39.848 | 32.227 | 22.562 | 14.016 | 10.921 |
| DTBP | 2.834 | 2.824 | 2.641 | 1.632 | 0.272 |

TABLE VI
SIMULTANEOUS DECOMPOSITION OF DTBP AND PREPARATION OF MTBE

| | | | | | |
|---|---|---|---|---|---|
| NOTEBOOK NUMBER | 6773-16-Q | 6773-86-1 | 6773-86-2 | 6773-86-3 | 6773-86-4 |
| CATALYST | | Fe Cu Cr on LZ-Y62 | Fe Cu Cr on LZ-Y62 | Fe Cu Cr on LZ-Y62 | Fe Cu Cr on LZ-Y62 |
| REACTOR (CC) | | 100 | 100 | 100 | 100 |
| PRESSURE (PSIG) | | 500 | 500 | 500 | 500 |
| FEED RATE (cc/Hr.) | | 100 | 100 | 100 | 100 |
| TEMPERATURE (C.) | | 120 | 140 | 160 | 180 |
| TIME ON STREAM (HR) | | 4 | 4 | 4 | 4 |
| SPACE VEL. (cc/cc) | | 1.0 | 1.0 | 1.0 | 1.0 |
| DTBP CONV. (%) | | 53.2 | 83.5 | 99.6 | 99.9 |
| TBA CONVERSION (%) | | 6.3 | 34.6 | 65.2 | 71.0 |
| IC$_4$H$_8$ | 0.004 | 0.773 | 2.261 | 3.539 | 2.826 |
| MEOH | 55.631 | 55.010 | 53.749 | 53.883 | 59.121 |
| ACETONE | 0.000 | 0.283 | 0.525 | 0.647 | 0.760 |
| MTBE | 1.213 | 4.834 | 16.149 | 26.927 | 23.878 |
| TBA | 40.024 | 37.521 | 26.168 | 13.937 | 11.600 |
| DTBP | 2.765 | 1.295 | 0.456 | 0.011 | 0.003 |
| NOTEBOOK NUMBER | 6773-16-Q | 6773-87-1 | 6773-87-2 | 6773-87-3 | 6773-87-4 |
| CATALYST | | Fe Cu Cr on LZ-Y62 | Fe Cu Cr on LZ-Y62 | Fe Cu Cr on LZ-Y62 | Fe Cu Cr on LZ-Y62 |
| REACTOR (CC) | | 100 | 100 | 100 | 100 |
| PRESSURE (PSIG) | | 500 | 500 | 500 | 500 |
| FEED RATE (cc/Hr.) | | 200 | 200 | 200 | 200 |
| TEMPERATURE (C.) | | 120 | 140 | 160 | 180 |
| TIME ON STREAM (HR) | | 4 | 4 | 4 | 4 |
| SPACE VEL. (cc/cc) | | 2.0 | 2.0 | 2.0 | 2.0 |
| DTBP CONV. (%) | | 15.1 | 54.5 | 94.4 | 99.6 |
| TBA CONVERSION (%) | | 3.0 | 22.9 | 57.5 | 72.0 |

TABLE VI-continued

| | | | | | |
|---|---|---|---|---|---|
| IC$_4$H$_8$ | 0.004 | 0.333 | 1.735 | 2.706 | 1.846 |
| MEOH | 55.631 | 55.591 | 54.506 | 54.157 | 58.650 |
| ACETONE | 0.000 | 0.098 | 0.308 | 0.707 | 1.121 |
| MTBE | 1.213 | 2.673 | 10.787 | 23.744 | 24.304 |
| TBA | 40.024 | 38.808 | 30.855 | 17.030 | 11.217 |
| DTBP | 2.765 | 2.347 | 1.257 | 0.156 | 0.010 |

| SIMULTANEOUS DECOMPOSITION OF DTBP AND PREPARATION OF MTBE IN A CONTINUOUS REACTOR | | | | | |
|---|---|---|---|---|---|
| NOTEBOOK NUMBER | 6773-16-Q | 6773-88-1 | 6773-88-2 | 6773-88-3 | 6773-88-4 |
| CATALYST | | Fe Cu Cr on LZ-Y62 | Fe Cu Cr on LZ-Y62 | Fe Cu Cr on LZ-Y62 | Fe Cu Cr on LZ-Y62 |
| REACTOR (CC) | | 100 | 100 | 100 | 100 |
| PRESSURE (PSIG) | | 500 | 500 | 500 | 500 |
| FEED RATE (cc/Hr.) | | 400 | 400 | 400 | 400 |
| TEMPERATURE (C.) | | 120 | 140 | 160 | 180 |
| TIME ON STREAM (HR) | | 4 | 4 | 4 | 4 |
| SPACE VEL. (cc/cc) | | 4.0 | 4.0 | 4.0 | 4.0 |
| DTBP CONV. (%) | | 0.0 | 11.6 | 60.9 | 96.1 |
| TBA CONVERSION (%) | | 2.3 | 20.4 | 49.3 | 67.3 |
| IC$_4$H$_8$ | 0.004 | 0.191 | 1.641 | 2.591 | 1.005 |
| MEOH | 55.631 | 55.862 | 54.798 | 54.208 | 58.397 |
| ACETONE | 0.000 | 0.026 | 0.159 | 0.608 | 1.080 |
| MTBE | 1.213 | 1.901 | 8.759 | 19.415 | 22.943 |
| TBA | 40.024 | 39.111 | 31.845 | 20.289 | 13.069 |
| DTBP | 2.765 | 2.804 | 2.443 | 1.080 | 0.108 |

TABLE VII

| SIMULTANEOUS DECOMPOSITION OF DTBP AND PREPARATION OF MTBE IN A CONTINUOUS REACTOR | | | | | |
|---|---|---|---|---|---|
| NOTEBOOK NUMBER | 6773-16-Q | 6773-89-1 | 6773-89-2 | 6773-89-3 | 6773-89-4 |
| CATALYST | | Co Mn on LZ-Y62 | Co Mn on LZ-Y62 | Co Mn on LZ-Y62 | Co Mn on LZ-Y62 |
| REACTOR (CC) | | 100 | 100 | 100 | 100 |
| PRESSURE (PSIG) | | 500 | 500 | 500 | 500 |
| FEED RATE (cc/Hr.) | | 100 | 100 | 100 | 100 |
| TEMPERATURE (C.) | | 120 | 140 | 160 | 180 |
| TIME ON STREAM (HR) | | 4 | 4 | 4 | 4 |
| SPACE VEL. (cc/cc) | | 1.0 | 1.0 | 1.0 | 1.0 |
| DTBP CONV. (%) | | 11.6 | 49.7 | 93.6 | 99.7 |
| TBA CONVERSION (%) | | 2.7 | 25.4 | 54.2 | 72.6 |
| IC$_4$H$_8$ | 0.004 | 0.219 | 1.190 | 2.301 | 2.424 |
| MEOH | 55.631 | 55.233 | 54.388 | 53.492 | 59.924 |
| ACETONE | 0.000 | 0.134 | 0.521 | 1.020 | 1.420 |
| MTBE | 1.213 | 2.812 | 11.547 | 22.391 | 22.804 |
| TBA | 40.024 | 38.950 | 29.868 | 18.318 | 10.954 |
| DTBP | 2.765 | 2.444 | 1.390 | 0.176 | 0.009 |
| NOTEBOOK NUMBER | 6773-16-Q | 6773-90-1 | 6773-90-2 | 6773-90-3 | 6770-90-4 |
| CATALYST | | Co Mn on LZ-Y62 | Co Mn on LZ-Y62 | Co Mn on LZ-Y62 | Co Mn on LZ-Y62 |
| REACTOR (CC) | | 100 | 100 | 100 | 100 |
| PRESSURE (PSIG) | | 500 | 500 | 500 | 500 |
| FEED RATE (cc/Hr.) | | 200 | 200 | 200 | 200 |
| TEMPERATURE (C.) | | 120 | 140 | 160 | 180 |
| TIME ON STREAM (HR) | | 4 | 4 | 4 | 4 |
| SPACE VEL. (cc/cc) | | 2.0 | 2.0 | 2.0 | 2.0 |
| DTBP CONV. (%) | | 7.6 | 29.3 | 99.0 | 99.7 |
| TBA CONVERSION (%) | | 4.9 | 27.1 | 68.9 | 73.0 |
| IC$_4$H$_8$ | 0.004 | 0.447 | 1.764 | 1.095 | 1.872 |
| MEOH | 55.631 | 55.556 | 54.551 | 57.045 | 60.988 |
| ACETONE | 0.000 | 0.064 | 0.279 | 1.391 | 1.713 |
| MTBE | 1.213 | 3.165 | 11.694 | 25.331 | 21.918 |
| TBA | 40.024 | 38.082 | 29.184 | 12.452 | 10.825 |
| DTBP | 2.765 | 2.554 | 1.954 | 0.027 | 0.009 |
| NOTEBOOK NUMBER | 6773-16-Q | 6773-91-1 | 6773-91-2 | 6773-91-3 | 6773-91-4 |
| CATALYST | | Co Mn on LZ-Y62 | Co Mn on LZ-Y62 | Co Mn on LZ-Y62 | Co Mn on LZ-Y62 |
| REACTOR (CC) | | 100 | 100 | 100 | 100 |
| PRESSURE (PSIG) | | 500 | 500 | 500 | 500 |
| FEED RATE (cc/Hr.) | | 400 | 400 | 400 | 400 |
| TEMPERATURE (C.) | | 120 | 140 | 160 | 180 |
| TIME ON STREAM (HR) | | 4 | 4 | 4 | 4 |
| SPACE VEL. (cc/cc) | | 4.0 | 4.0 | 4.0 | 4.0 |
| DTBP CONV. (%) | | 3.0 | 13.7 | 76.5 | 95.2 |
| TBA CONVERSION (%) | | 2.3 | 21.1 | 62.3 | 69.1 |
| IC$_4$H$_8$ | 0.004 | 0.227 | 1.613 | 1.380 | 0.867 |
| MEOH | 55.631 | 55.651 | 54.872 | 57.236 | 61.170 |

TABLE VII-continued

SIMULTANEOUS DECOMPOSITION OF DTBP AND PREPARATION OF MTBE IN A CONTINUOUS REACTOR

| ACETONE | 0.000 | 0.032 | 0.136 | 0.986 | 1.303 |
|---------|-------|-------|-------|-------|-------|
| MTBE    | 1.213 | 2.204 | 9.056 | 22.568 | 21.588 |
| TBA     | 40.024 | 39.098 | 31.584 | 15.093 | 12.383 |
| DTBP    | 2.765 | 2.683 | 2.387 | 0.649 | 0.134 |

EXAMPLE 12

Using the equipment and following the procedures of Example 5, the Fe, Cu, Cr on VALFOR® CP316-26 catalyst of Example 1 was treated with a crude, 2:1 molar, mix of methanol to t-butanol feedstock that also contained significant quantities of MTBE, water, isopropanol (2-PrOH), acetone ($Ac_2O$), di-t-butyl peroxide (DTBP) and t-butyl formate (TBF). Etherification was conducted at 140° C., 300 psi using a LHSV of 2.

Concentrations of each of these components, plus isobutylene, in the product effluent were determined by glc. Typical data are given in the accompanying Table VIII.

Of particular note, under these operating conditions:

| TBA Conversion | 73% |
|---|---|
| MTBE Selectivity | 70% |
| Isobutylene Selectivity | 25% |
| Di-t-butyl peroxide Decomposition | 55% |

TABLE VIII

| | | | | ←MTBE From MEOH/TBA→ PRODUCT COMPOSITION | | | | | | | |
|---|---|---|---|---|---|---|---|---|---|---|---|
| Ex. | Catalyst | Sample | $H_2O$ | MeOH | $C_4H_8$ | $Ac_2O$ | 2-PrOH | TBA | MTBE | DTBP | TBF |
| 12 | Ex. 1 | FS-1 | 5.0 | 40.2 | | 0.6 | 1.4 | 50.9 | 2.0 | 4.4 | 0.2 |
| | | 1 | 14.0 | 29.6 | 6.9 | 1.3 | 2.3 | 13.8 | 32.7 | 2.0 | 0.01 |

What is claimed is:

1. In a method wherein t-butanol is reacted with methanol in one-step in the presence of a catalyst to provide methyl tert-butyl ether, the improvement of using as a catalyst a zeolite-modified with multimetals selected from Groups IB, VB, VIB, VIIB, VIII of the Periodic Table and continuously contacting said methanol and t-butanol in a molar amount of from about 10:1 to 1:10 over said zeolite catalyst at a temperature of about 20° C. to about 250° C. and a pressure of about atmospheric to about 1000 psig to obtain methyl tert-butyl ether product.

2. The method of claim 1 wherein the zeolite is selected from the group consisting of zeolite-Y and zeolite-X.

3. The method of claim 2 wherein the zeolite is a Y-zeolite.

4. The method of claim 3 wherein the zeolite further comprises a rare-earth exchanged Y-zeolite.

5. The method of claim 3 wherein the zeolite further comprises an ammonium exchanged Y-zeolite.

6. The method of claim 3 wherein the zeolite further comprises an ammonium exchanged Y-zeolite having a Si:Al ratio in the range 3 to 100.

7. The method of claim 1 wherein the zeolite is modified with iron, copper, chromium, manganese and cobalt.

8. The method of claim 1 wherein the zeolite is modified with iron, copper and chromium.

9. The method of claim 1 wherein the zeolite is modified with nickel, copper and chromium.

10. The method of claim 1 wherein the zeolite is modified with cobalt and manganese.

11. The method of claim 1 wherein the temperature is from about 80° C. to about 200° C.

12. The method of claim 1 wherein the operating temperature is in the range of about 160° C. to 200° C. and the product comprises a two-phase mix of an isobutylene-MTBE product-rich phase and a heavier aqueous methanol-rich phase.

13. The method of claim 1 wherein the t-butanol and methanol reactants also contain a peroxide fraction.

14. The method of claim 13 wherein the peroxide fraction is selected from the group consisting of di-t-butyl peroxide, allyl t-butyl peroxide and t-butylhydroperoxide.

15. The method of claim 14 wherein said peroxide fractions are decomposed over a metals-modified zeolite concurrently with the formation of methyl tert-butyl ether.

16. The method of claim 15 wherein the zeolite catalyst is an ammonium-exchanged Y-zeolite modified with the metals iron, copper and chromium.

17. The method of claim 15 wherein the zeolite catalyst is an ammonium-exchanged Y-zeolite modified with the metals cobalt and manganese.

18. The method of claim 15 wherein the zeolite catalyst is a rare-earth exchanged zeolite modified with the metals nickel, copper and chromium.

19. The method of claim 15 wherein the zeolite catalyst is an ammonium-exchanged Y-zeolite modified with the metals nickel, copper and chromium.

20. The method of claim 15 wherein the concentrations of metals deposited on said zeolite may vary from 0.01% to 10.0% for each metal.

* * * * *